US00PP21549P2

(12) United States Plant Patent
Ulate

(10) Patent No.: US PP21,549 P2
(45) Date of Patent: Nov. 30, 2010

(54) ***DRACAENA* PLANT NAMED 'LAUREN'**

(50) Latin Name: *Dracaena deremensis*
Varietal Denomination: Lauren

(75) Inventor: William Vasquez Ulate, Alajuela (CR)

(73) Assignee: Florica Farms, Inc., Eustis, FL (US)

( * ) Notice: Subject to any disclaimer, the term of this patent is extended or adjusted under 35 U.S.C. 154(b) by 0 days.

(21) Appl. No.: 12/462,751

(22) Filed: Aug. 7, 2009

(51) Int. Cl.
*A01H 5/00* (2006.01)

(52) U.S. Cl. ..... Plt./383

(58) Field of Classification Search ..... Plt./383
See application file for complete search history.

*Primary Examiner*—June Hwu
*Assistant Examiner*—Louanne C Krawczewicz Myers
(74) *Attorney, Agent, or Firm*—Foley & Lardner LLP

(57) ABSTRACT

A new and distinct *Dracaena deremensis* plant named 'LAUREN' particularly characterized by its green leaves, closest to RHS 137A, with distinct green-white variegated streaks, closest to RHS 157A and RHS 157B, running longitudinally parallel (streaks same on front and back of leaf); leaves measuring about 35 cm to 45 cm in length and slightly pendulous in overall shape; annual growth rate of about 50 cm; strong, thick stem, measuring about 2 cm to 4 cm in diameter and yellow-green in color, closest to RHS 145C and RHS 145D; and plant height of about 185 cm and plant spread of about 55 cm to 75 cm, when grown in 35 cm size container.

3 Drawing Sheets

Latin name of the genus and species of the claimed plant: *Dracaena deremensis.*

Variety denomination: 'LAUREN'.

BACKGROUND OF THE INVENTION

The present invention relates to a new and distinct cultivar of *Dracaena* plant, botanically known as *Dracaena deremensis,* of the family *Agavaceae*, hereinafter referred to by the cultivar name 'LAUREN'.

*Dracaena* is a monocotyledonous tropical foliage plant which can be produced as a single or multi-stemmed plant for interior use or outdoors in shade in zones 9 or 10 only.

The new *Dracaena* 'LAUREN' originated from a naturally occurring branch mutation of *Dracaena deremensis* 'DR9901ART' (patented, U.S. Plant Pat. No. 13,814). The new *Dracaena* 'LAUREN' was discovered and selected by the inventor, William Vasquez Ulate, in June of 2006 as a single plant within the progeny of the stated mutation in a controlled environment in Palmares, Alajuela, Costa Rica.

Asexual reproduction of the new *Dracaena* by vegetative, air layer, or rooted cuttings was first performed in June of 2006 in Palmares, Alajuela, Costa Rica, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'LAUREN', which in combination distinguish this *Dracaena* as a new and distinct cultivar:

1. Green leaves, closest to RHS 137A, with distinct green-white variegated streaks, closest to RHS 157A and RHS 157B, running longitudinally parallel (streaks same on front and back of leaf);

2. Leaves measuring about 35 cm to 45 cm in length and slightly pendulous in overall shape;
3. Annual growth rate of about 50 cm;
4. Strong, thick stem, measuring about 2 cm to 4 cm in diameter and yellow-green in color, closest to RHS 145C and RHS 145D; and
5. Plant height of about 185 cm and plant spread of about 55 cm to 75 cm, when grown in 35 cm size container.

Plants of the new *Dracaena* 'LAUREN' differ from plants of the parental cultivar, *Dracaena deremensis* 'DR9901ART' (patented, U.S. Plant Pat. No. 13,814) in the characteristics described in Table 1.

TABLE 1

| Characteristic | New Cultivar *Dracaena deremensis* 'LAUREN' | Parental Cultivar *Dracaena deremensis* 'DR9901ART' U.S. Plant Pat. No. 13,814 |
|---|---|---|
| Mature Leaf color (Upper side) | Overall background green, closest to RHS 137A, with variegated green-white streaks, closest to RHS 157A and RHS 157B. Margin is yellow-green, RHS 144A. | Green leaves, closest to but between RHS 137A and RHS 139A, with yellow-green margins, RHS 144A to RHS 144B |
| Leaf thickness | Thicker, $1/64^{th}$ inch | Thinner, $1/100^{th}$ inch |
| Leaf texture | More leathery and more ribbed | Less leathery and less ribbed |
| Stem thickness | Thicker, 0.5 to 1.5 inch | Thinner, 0.25 to 1.25 inch |
| Stem color | A blend of yellow-green, closest to RHS 145C and RHS 145D.The clasping nature of leaves gives the stem a variegated appearance. | Green, darker than RHS 139A,with yellow-green margins |
| Internodes | Closer internodes at 1 cm to 2 cm | Farther internodes at 2 cm to 3 cm |

Of the many commercial cultivars known to the present inventor, the most similar in comparison to the new *Dracaena* 'LAUREN' is the parental cultivar, *Dracaena deremensis*

'DR9901ART' (patented, U.S. Plant Pat. No. 13,814) as described in the foregoing Table 1.

BRIEF DESCRIPTION OF THE PHOTOGRAPHS

The accompanying photographs illustrate the overall appearance of the new *Dracaena* 'LAUREN' showing the colors as true as is reasonably possible with colored reproductions of this type. Colors in the photographs may differ slightly from the color value cited in the detailed botanical description which accurately describes the color of 'LAUREN'. The accompanying photographs show the distinctive green-white variegated foliage streaks of a mature, typical plant of 'LAUREN', following growth under appropriate growing conditions with colors being as true as possible with illustrations of this type.

DETAILED BOTANICAL DESCRIPTION

Figure 1:
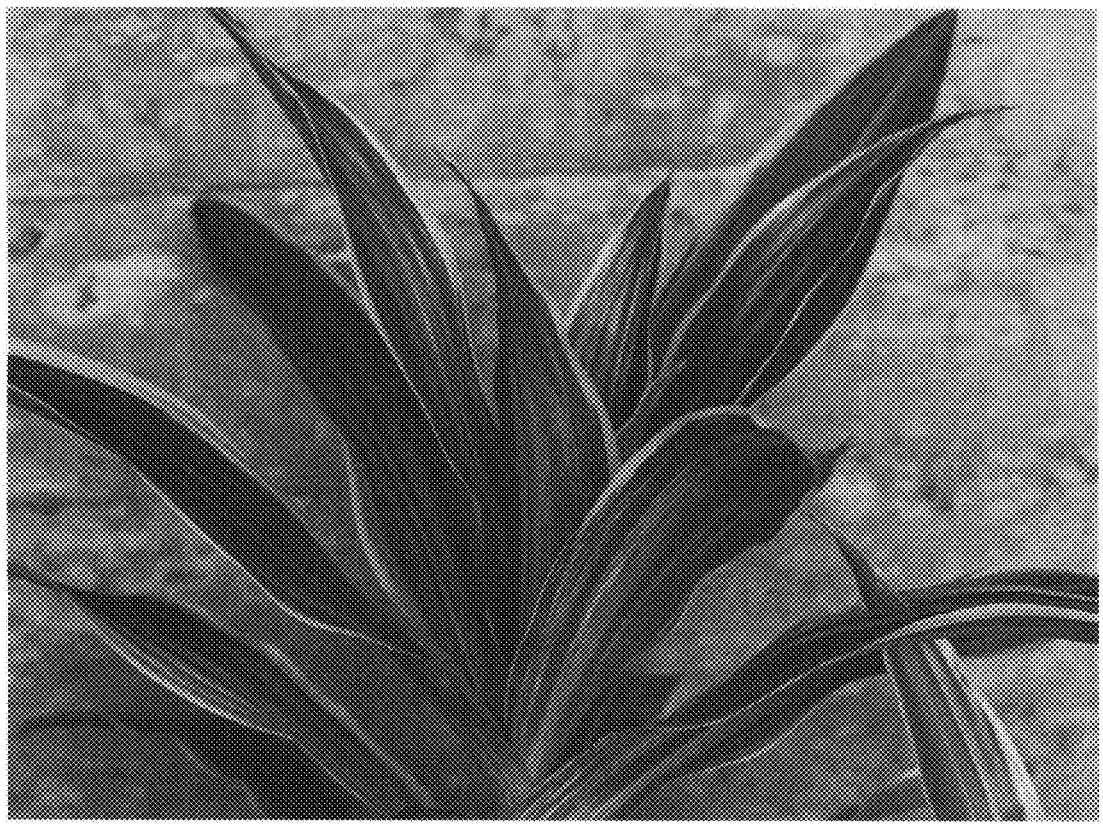
FIG. 1 shows a side view perspective of a typical plant of 'LAUREN' in a 26 cm pot, at 3 months of age.
Figure 2:
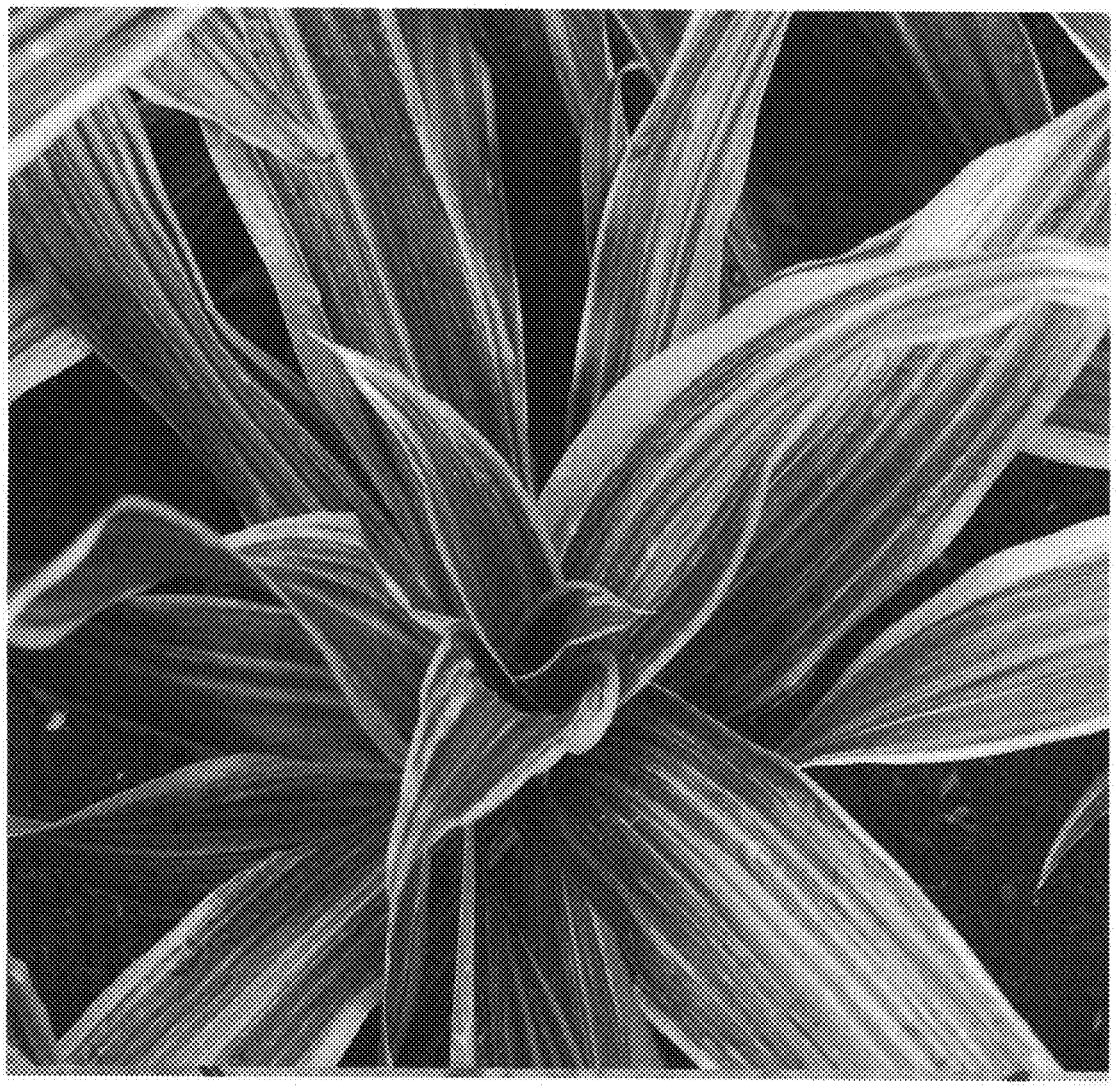
FIG. 2 shows a top view perspective of a typical plant of 'LAUREN' in a 26 cm pot, at 3 months of age.
Figure 3:
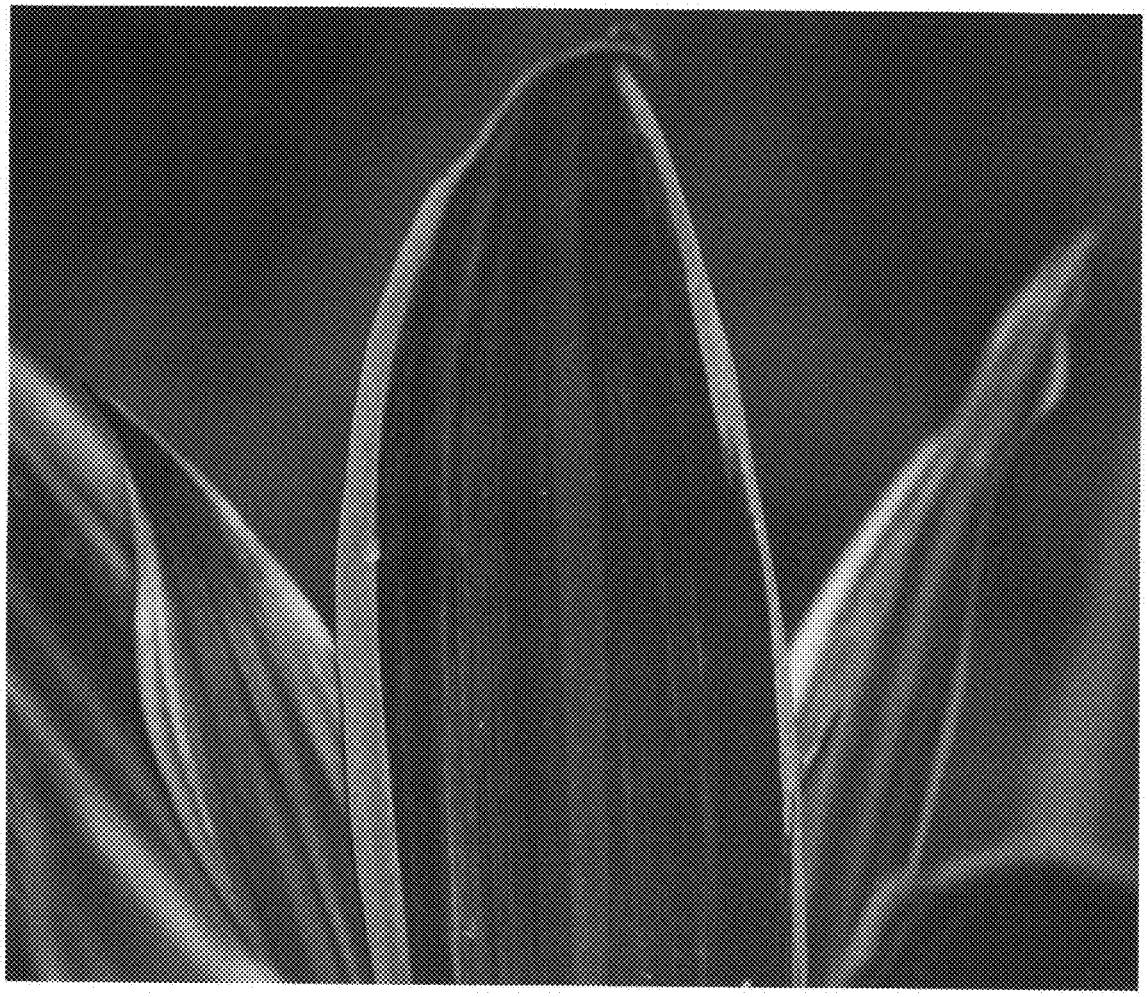
FIG. 3 shows a close-up view of the typical leaves of 'LAUREN' at 3 months of age.

The new *Dracaena* 'LAUREN' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Dracaena* 'LAUREN' as grown in a polyethylene-covered greenhouse in Apopka, Fla., under conditions which closely approximate those generally used in commercial practice. Plants of the new *Dracaena* 'LAUREN' are grown with an average day temperature of 90° F. and an average night temperature of 75° F. Plants of the new *Dracaena* 'LAUREN' are grown under light conditions of about 80% shade from natural sunlight and about 80% relative humidity. Plants of the new *Dracaena* 'LAUREN' are applied 1) a liquid 24-8-16 fertilizer weekly, and 2) a granular Nutricote 18-6-12 fertilizer every 100 days. No growth retardants are used when growing plants of the new *Dracaena* 'LAUREN'.

Color references are made to The Royal Horticultural Society Colour Chart (R.H.S.), 2001 edition except where general colors of ordinary significance are used. The photographs and descriptions were taken during the summer season of 2009 in Apopka, Fla., when outdoor day temperatures averaged 90° F. and outdoor night temperatures averaged 75° F. The age of the plants described is 3 months, after planted from rooted cuttings.

Classification:

*Botanical.*—*Dracaena deremensis.*

Parentage: *Dracaena deremensis* 'DR9901ART' (patented, U.S. Plant Pat. No. 13,814)

Optimal growth conditions:

*Light intensities.*—80% shade.

*Temperature.*—Day: Range of 75° F. to 95° F.; average 85° F.; Night: 75° F. to 85° F.; average 80° F.

*Temperature tolerance.*—Tolerant to a low temperature of about 50° F. and tolerant to a high temperature of about 100° F.

*Fertilization.*—A liquid 24-8-16 fertilizer weekly, and a granular Nutricote 18-6-12 fertilizer every 100 days.

*Growth regulators.*—None.

Propagation:

*Type.*—Vegetative, by air layer or rooted cuttings.

*Rooting habit and description.*—Easy to root. Roots are mostly fibrous and finely branched. New emerging roots are white, RHS 155, and mature roots are greyed-orange, RHS 165B and RHS 165C.

*Time to initiate roots.*—About 10 to 15 days at 80° F.

*Time to produce a rooted cutting.*—About 30 to 45 days at 80° F.

Plant:

*General appearance and form.*—Height: About 300 cm when grown in ground; About 185 cm when grown in a 35 cm size container. Spread: About 65 cm to 90 cm (single stem) when grown in ground; About 55 cm to 75 cm when grown in 35 cm size container. Form: Monocot; leaves whorled, leaf bases wrap around the stem. Shape: Round.

*Growth rate and habit.*—About 50 cm annually; upright.

*Fragrance.*—None.

*Stem.*—Quantity per plant: About 3 per 26 cm container; about 4 per 35 cm container. Length: About 300 cm when grown in ground; About 185 cm when grown in 35 cm size container. Diameter: About 2 cm to 4 cm. Shape: Cylindrical. Texture: Thick (waxy and rubbery) and ribbed. Color: Yellow-green, RHS 145C and 145D. Strength: Strong. Internode length: About 1 cm to 2 cm.

Foliage:

*Quantity.*—About 25 leaves per stem at 80 cm.

*Arrangement and attachment.*—Single, alternate; leaves whorled; leaf bases wrap around the stem.

*Leaf length.*—About 35 cm to 45 cm.

*Leaf width.*—About 6 cm to 10 cm.

*Overall shape of leaf.*—Slightly pendulous, lanceolate.

*Apex shape.*—Acuminate.

*Base shape.*—Sheathing.

*Margin.*—Entire, slightly undulate, leaf rolled ½ cm at apex.

*Margin color.*—Yellow-green, RHS 144A.

*Texture.*—Upper and Under Surfaces: Leathery, longitudinally, lustrous, furrowed at main vein.

*Pubescence.*—None.

*Color of mature and immature leaf upper and under surfaces.*—Overall background green, closest to RHS 137A with variegated green-white streaks, closest to RHS 157A and RHS 157B. Margin is yellow-green, RHS 144A. Variegated streaks longitudinally extend the entire leaf and are the same on the upper and under surfaces.

*Venation.*—Pattern: Several longitudinally, variegated streaks parallel to leaf veins, main vein furrowed. Color: Upper and under surfaces: Green-white, RHS 157A to 157B.

*Leaf fragrance.*—None.

Inflorescence description: No flowering observed.

Reproductive organs: No reproductive organs observed.

Disease/pest resistance: Resistance, tolerance and susceptibility to stresses, pathogens and pests is very good.

Disease/pest susceptibility: Resistance, tolerance and susceptibility to stresses, pathogens and pests is very good.

What is claimed is:

1. A new and distinct *Dracaena deremensis* plant named 'LAUREN', substantially as illustrated and described herein.

* * * * *